United States Patent
Walk et al.

(10) Patent No.: US 11,324,670 B2
(45) Date of Patent: May 10, 2022

(54) COCOA BUTTER POWDERED MOISTURIZER

(71) Applicants: Bilal Walk, East Point, GA (US); Elizabeth Handy, East Point, GA (US)

(72) Inventors: Bilal Walk, East Point, GA (US); Elizabeth Handy, East Point, GA (US)

( * ) Notice: Subject to any disclaimer, the term of this patent is extended or adjusted under 35 U.S.C. 154(b) by 0 days.

(21) Appl. No.: 14/516,513

(22) Filed: Oct. 16, 2014

(65) Prior Publication Data

US 2016/0106662 A1 Apr. 21, 2016
US 2021/0052484 A9 Feb. 25, 2021

Related U.S. Application Data

(60) Provisional application No. 61/891,498, filed on Oct. 16, 2013.

(51) Int. Cl.
| | |
|---|---|
| A61K 8/97 | (2017.01) |
| A61K 8/02 | (2006.01) |
| A61Q 19/00 | (2006.01) |
| A61K 8/92 | (2006.01) |
| A61K 8/9789 | (2017.01) |

(52) U.S. Cl.
CPC ............ *A61K 8/0225* (2013.01); *A61K 8/922* (2013.01); *A61K 8/97* (2013.01); *A61K 8/9789* (2017.08); *A61Q 19/00* (2013.01); *A61K 2800/805* (2013.01); *A61K 2800/87* (2013.01)

(58) Field of Classification Search
None
See application file for complete search history.

(56) References Cited

U.S. PATENT DOCUMENTS

| | | | | |
|---|---|---|---|---|
| 4,308,288 A | * | 12/1981 | Hara ...................... | A23G 1/047 426/285 |
| 5,017,367 A | | 5/1991 | Stojkoski et al. | |
| 5,731,000 A | * | 3/1998 | Ruff ..................... | A61K 9/2013 424/434 |
| 6,165,518 A | * | 12/2000 | Cain ........................ | A21D 2/16 426/554 |
| 7,842,322 B2 | * | 11/2010 | Manning .................. | A23G 1/56 426/442 |

(Continued)

FOREIGN PATENT DOCUMENTS

| | | | |
|---|---|---|---|
| EP | 2127636 | | 12/2009 |
| FR | 2929850 | * | 4/2008 |
| GB | 190313713 A | * | 5/1904 |

(Continued)

OTHER PUBLICATIONS

Vitacost, "Queen Helene 100% Cocoa Butter Moisturizer Stick", Jan. 18, 2010.*

(Continued)

*Primary Examiner* — Jianfeng Song
(74) *Attorney, Agent, or Firm* — Stonebridge IP, PLLC

(57) ABSTRACT

The present invention is a cocoa butter powdered moisturizer with the addition of cocoa powder serving as a stabilizing agent. The cocoa butter is grated and/or shredded into a fine granulated form and is supplemented with the stabilizing cocoa powder such that the resulting moisturizer attains a consistent, usable form. The resulting moisturizer is stable at room temperature and provides an SPF-15 level of sun protection for the skin.

6 Claims, 4 Drawing Sheets

(56) References Cited

U.S. PATENT DOCUMENTS

| | | | |
|---|---|---|---|
| 8,075,901 B1 | 12/2011 | Waters | |
| 2011/0060039 A1 * | 3/2011 | Bernaert | ................ A61P 17/00 |
| | | | 514/456 |

FOREIGN PATENT DOCUMENTS

| | | | | |
|---|---|---|---|---|
| JP | 06212170 | * | 8/1994 | |
| JP | 2004-018498 | * | 1/2004 | |
| JP | 3174543 | * | 3/2012 | |
| KR | 2012134956 | * | 12/2012 | |
| WO | WO199108059 | * | 6/1991 | |
| WO | WO-02087351 A1 | * | 11/2002 | .............. A23G 1/36 |
| WO | WO2003090670 | | 12/2003 | |
| WO | WO2011159439 | | 7/2013 | |

OTHER PUBLICATIONS

Cocoa Butter Lotion, Product Advertisement, Now(TM) Solutions, Aug. 11, 2014.
Too Faced, Cocoa Powder Foundation, Product advertisement, Sephora(TM), Aug. 11, 2014.

\* cited by examiner

COCOA BUTTER POWDERED MOISTURIZER

CLAIM OF PRIORITY

This application claims the benefit of priority to the provisional patent application No. 61/891,498, filed Oct. 16, 2013 and entitled "Cocoa Butter-Powered Moisturizer", which is incorporated herein by reference.

COPYRIGHT AND TRADEMARK NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever. Trademarks are the property of their respective owners.

BACKGROUND

The present invention relates generally to skincare products, primarily moisturizing products. Many moisturizing products do not penetrate through all of the layers of skin; and, even when they do, may contain chemicals that are not used in the action of moisturizing the skin, but rather are stabilizers and other chemicals to preserve shelf life, or the look and feel of the product. These chemicals are directed more to enticing buyers to purchase, such as fragrances, than they are to the task of moisturizing the buyers skin. Additionally, buyers who have skin conditions such as eczema or dermatitis must be very cautious about the chemical formulation of a skin moisturizer or suffer the possible worsening of their skin condition.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

Figure 1:
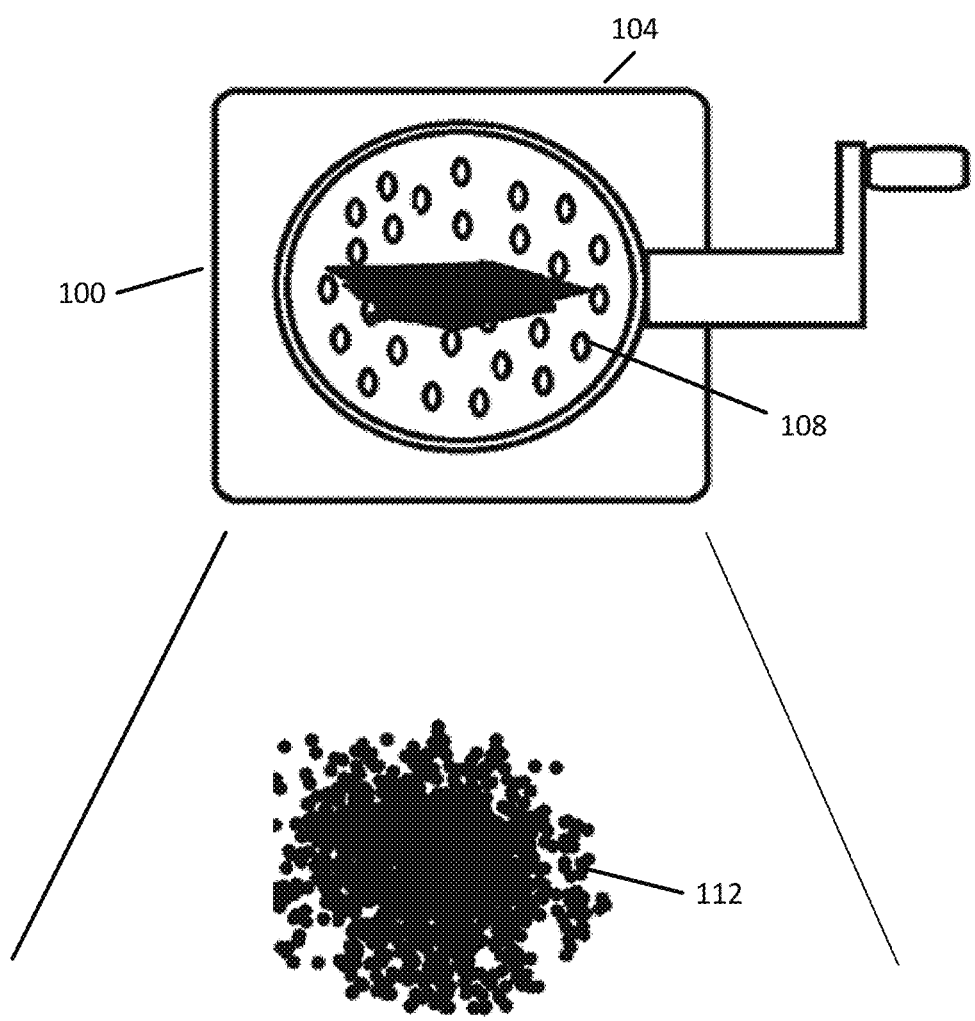
FIG. 1 is a representation of the grating of cocoa butter into a shredded form consistent with certain embodiments of the present invention.

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an exemplary embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to cocoa butter refers to a cream-colored vegetable fat that is extracted from cacao seeds and is used in a wide variety of applications.

Reference throughout this document to cocoa powder refers to the remaining solid components following extraction of cocoa butter from cacao beans. The remaining components are generally processed into cocoa powder following cleaning, roasting, and pressing of the cacao beans to extract the cocoa butter from the beans.

The present invention relates generally to skincare products, primarily moisturizing products. More specifically, the present invention is a cocoa butter powdered moisturizer with the addition of cocoa powder serving as a stabilizing agent. The cocoa butter is grated and/or shredded into a fine granulated form and is supplemented with the stabilizing cocoa powder such that the resulting moisturizer attains a consistent, usable form.

While cocoa butter is widely utilized to create chocolate, cocoa butter is also renowned for its personal care benefits. The benefits of cocoa butter as a personal care product are perhaps most prominent in skincare. Cocoa butter is renowned for its emollient properties and as such is utilized in order to moisturize often severely dry and itchy skin. Once applied, cocoa butter absorbs quickly into the skin and assists in retaining moisture in the skin and as such is often preferred over the more common petroleum-based moisturizers. Unlike many other types of moisturizers, cocoa butter penetrates deep through multiple layers of skin and as such is one of the most effective remedies for excessively dry skin. Cocoa butter greatly facilitates moisture retention, eliminating the need to constantly reapply the cocoa butter throughout the day. The cocoa butter provides a barrier between a user's skin and the exterior environment and is thus useful for alleviating the symptoms of skin conditions such as eczema and dermatitis. In addition to these medical benefits, cocoa butter contains a variety of different minerals and antioxidants that are ideal for skincare. In particular, cocoa butter is rich in calcium, potassium, magnesium, zinc, manganese, copper, and iron, as well as the strong antioxidant vitamin E. The high concentration of beneficial minerals and antioxidants assists in reducing premature aging of the skin as well as tissue damage. For example, cocoa butter has been shown to prevent or reduce stretch marks, particularly for pregnant women. While the benefits of cocoa butter as a moisturizer are widely recognized, pure cocoa butter may be difficult to utilize properly. When utilizing a cocoa butter bar, the cocoa butter may not melt upon coming into contact with the user's skin, creating difficulties in applying the cocoa butter to dry and itchy skin. This is often the case when the moisturizer bar contains additional ingredients along with the cocoa butter.

Additionally, a cocoa butter bar may become dirtied and contaminated over time due to continuous use. The present invention seeks to address the aforementioned issues as well as enhance and improve upon currently existing conventional cocoa butter skincare products.

The present invention is a cocoa butter powdered moisturizer in which cocoa powder is utilized as a stabilizing agent. In its preferred embodiment, the present invention comprises organic grated/shredded cocoa butter. The cocoa butter is unprocessed and 100% pure. However, if required, naturally present sediments may be sifted and removed from the cocoa butter. The grated/shredded cocoa butter serves as a base and is supplemented with cocoa powder. The cocoa butter is initially grated or shredded into a fine granulated form. The cocoa powder is added to the grated/shredded cocoa butter as a stabilizing agent. The fine granulated cocoa butter and cocoa powder are combined and mixed. The cocoa butter and cocoa powder are continuously and thoroughly mixed until the resulting moisturizer has gained usable form. The cocoa powder strengthens the integrity of the cocoa butter granules. As such, throughout and following the mixing process, the stabilizing cocoa powder prevents the individual granules of cocoa butter from clumping together. This facilitates the process of applying the moisturizer to the skin as the granules of the moisturizer melt upon coming into contact with the warm skin. The resulting moisturizer is stable at room temperature and provides an SPF-15 level of sun protection for the skin upon application. In the preferred embodiment of the present invention, the moisturizer is primarily intended for use with a dispenser. The dispenser increases sanitation and hygiene of users as the dispenser eliminates the need to possibly share a cocoa butter bar with possibly multiple additional users.

Turning to FIG. 1, this figure presents a representation of the grating of cocoa butter into a shredded form consistent with certain embodiments of the present invention. In an exemplary embodiment, the process begins with 100% prime pressed cocoa butter, which is in a solid form. The solid cocoa butter is then cut into smaller pieces 100. Each smaller piece 100 is then grated with a standard chocolate, hard cheese, or nut grater 104. The grating hole size 108 of the grater 104 is of a sufficient size to create a shredded powdered-like form 112 that is similar in consistency and granular size to a coarse grain flour.

Figure 2:
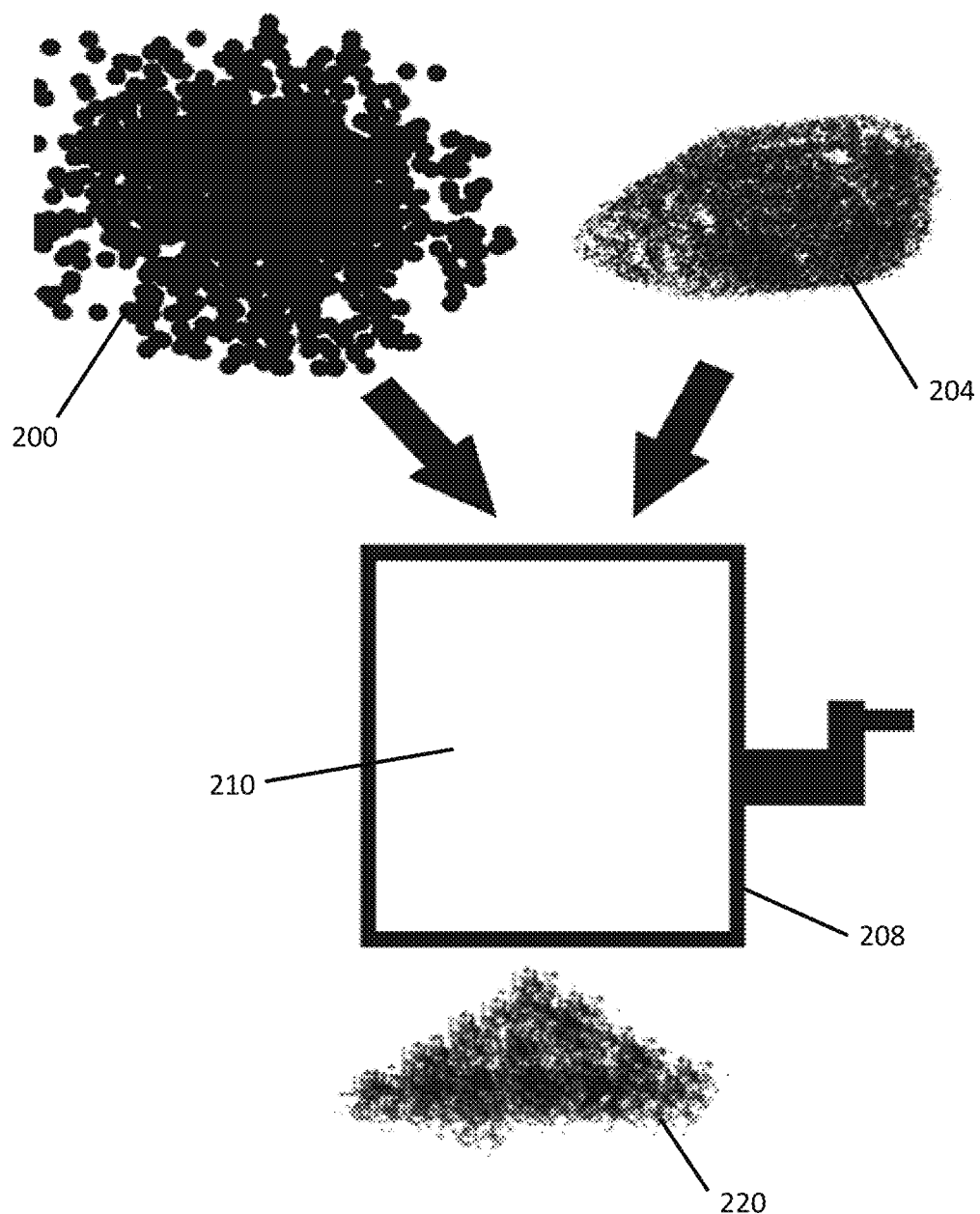
FIG. 2 is a representation of the sifting together of shredded cocoa butter and coco powder consistent with certain embodiments of the present invention.

Turning to FIG. 2, this figure presents a representation of the sifting together of shredded cocoa butter and coco powder consistent with certain embodiments of the present invention. In an embodiment, the shredded powdered form of the cocoa butter is measured into 16 ounce increments 200. Organic cocoa powder 204 is measured in two gram increments. In a non-limiting example, a 16 ounce increment 200 of the shredded cocoa butter is combined with a two gram increment of the organic cocoa powder 204 in a standard kitchen powder sifter 208. Operating the standard kitchen powder sifter 208, the 16 ounces of the shredded powdered cocoa butter 200 is sifted together with the 2 grams of organic cocoa powder 204. These portions represent just one batch size and should in no way be considered limiting to the process of combining the shredded cocoa butter with the cocoa powder. In a preferred embodiment the final product will maintain the desired properties when the ratio of 8 ounces of shredded cocoa butter to 1 gram of cocoa powder is maintained as additional batch sizes are created to produce larger amounts of the final product in each batch.

In this embodiment, organic cocoa powder is derived from the cocoa bean, and is created during the cocoa butter production process. In an non-limiting example, organic cocoa powder 204 is very light in form and being that cocoa butter and organic cocoa powder both come from the cocoa bean they share like elements in respect to composition as recited above. It will be understood by persons of ordinary skill in the art that organic cocoa powder is the preferred material for use in this process, however, non-organic cocoa powder may be used in alternative embodiments without deviating from the inventive process. During the sifting process, a preferential attraction between the organic cocoa powder 204 and the shredded powdered cocoa butter 200 causes the organic cocoa powder 204 to bond and lock in with the shredded powdered cocoa butter 200. During the sifting, the shredded powdered cocoa butter 200 and organic cocoa powder 204 attach to one another, with preferential attraction between the materials facilitating the bonding of the two materials. The sifter 208 separates and collects larger granulated pieces within the sifter body 210, producing a finished product of a fine powder substance 220 containing the combined materials that is a granular powder having a smooth texture.

In this embodiment, the fine powder substance 220 is solid, stable and yet readily dispensable as it flows readily as a fine powder, similar to talc in consistency and spreadability. The fine powder substance is a granular powder that is composed of shredded grains of cocoa butter coated with cocoa powder to create grains composed of a core of shredded cocoa butter coated by cocoa powder. The fine powder substance 220 may be used in this form as a moisturizer when placed upon the outer surface of human skin.

Figure 3:
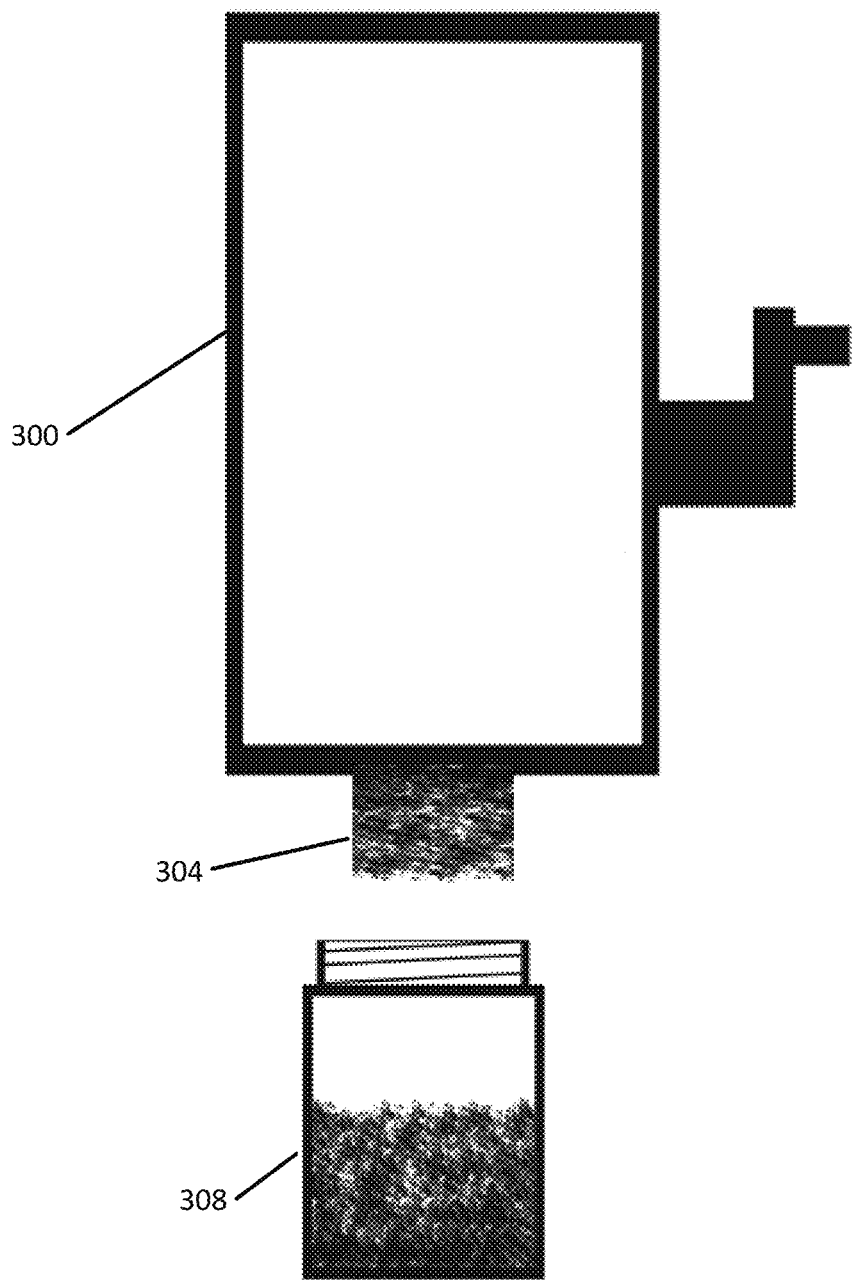
FIG. 3 is a representation of the packaging of the cocoa butter-powdered moisturizer consistent with certain embodiments of the present invention.

Turning now to FIG. 3 this figure presents a representation of the packaging of the cocoa butter-powdered moisturizer consistent with certain embodiments of the present invention. The materials are sifted together in a standard kitchen sifter 400 to produce a fine powder substance 404 that consists of granules of the shredded cocoa butter coated with the cocoa powder during the sifting process step. The fine powder substance 404 that may be used as a skin moisturizer is placed into small jar dispensers 408 that may dispense the granular powder either in measured portions or freely to the touch of a user.

Figure 4:
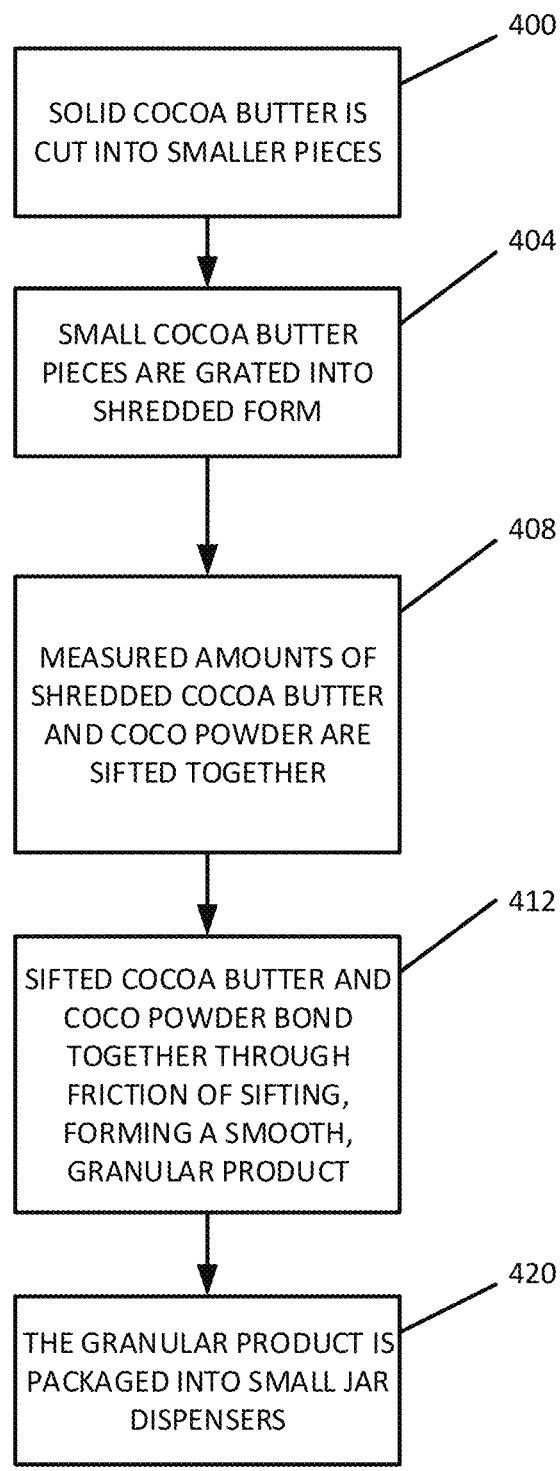
FIG. 4 is a flow diagram of the process of creating the cocoa butter-powdered moisturizer consistent with certain embodiments of the present invention.

Turning to FIG. 4, this figure presents a flow diagram of the process of creating the cocoa butter-powdered moisturizer consistent with certain embodiments of the present invention. In this exemplary process, at step 400 solid cocoa butter, which is derived from cocoa beans, is cut into smaller pieces for ease of use during this process. At step 404, the smaller cocoa butter pieces are grated using a standard chocolate, cheese, or nut grater into a shredded form. The shredded form may be a consistent size resembling coarse-ground grain flour. At step 408, the shredded cocoa butter and cocoa powder are measured into consistent size amounts. In a non-limiting example, the shredded cocoa butter is measured into 16 ounce portion and the cocoa powder is measured into a two gram portion. These portions represent just one batch size and should in no way be considered limiting to the process of combining the shredded cocoa butter with the cocoa powder as additional batch sizes may be utilized in the creation of the final product. The measured portions of shredded cocoa butter and the cocoa powder are then sifted together in a standard kitchen flour sifter.

In this non-limiting embodiment, at step 412 the sifting together of the shredded cocoa butter and the cocoa powder causes the materials to bond together through the preferential attraction and bonding of the materials as previously described. The shredded cocoa butter maintains a granulated form due to the bonding with the cocoa powder, which acts as an anti-clumping agent and prevents the cocoa butter from clumping or sticking back together after being sifted together. The materials continue to mix and bond together, with the shreds that are too large remaining in the body of the sifter as the mixed, bonded material emerges from the sifter. The resulting product is a smooth, granular product that is solid, stable and yet spreads readily, having a consistency much like talcum powder. The resulting product may be used as a moisturizer that is stable at room temperature and provides an SPF-15 level of sun protection for the skin. At 420, the smooth, granular product is packaged into small jar dispensers that are ready for sale to, and use by, customers.

While certain illustrative embodiments have been described, it is evident that many alternatives, modifications, permutations and variations will become apparent to those skilled in the art in light of the foregoing description.

What is claimed is:

1. A method of making a skincare product consisting of: combining cocoa butter granules and cocoa powder.

2. The method of claim 1, wherein the cocoa butter granules are prepared by shredding or grating cocoa butter.

3. The method of claim 1, wherein the cocoa butter granules and cocoa powder are combined by sifting.

4. The method of claim 1, wherein the cocoa butter granules and cocoa powder are combined in a ratio of about 1 gram of cocoa powder to about 8 ounces of cocoa butter granules.

5. The method of claim 1, wherein the cocoa powder is organic cocoa powder.

6. The method of claim 1, wherein the resulting cocoa butter granules and cocoa powder have a powder form and consistency, and include grains composed of a core of granular cocoa butter coated by cocoa powder.

* * * * *